United States Patent [19]

Dutcher et al.

[11] 4,357,946

[45] Nov. 9, 1982

[54] EPICARDIAL PACING LEAD WITH STYLET CONTROLLED HELICAL FIXATION SCREW

[75] Inventors: Robert G. Dutcher, Columbia Heights; Edward G. O'Neill, St. Paul, both of Minn.

[73] Assignee: Medtronic, Inc., Minneapolis, Minn.

[21] Appl. No.: 133,217

[22] Filed: Mar. 24, 1980

[51] Int. Cl.³ ............................................. A61N 1/04
[52] U.S. Cl. ................................. 128/785; 128/419 P
[58] Field of Search .................... 128/419 P, 784–786, 128/639, 642

[56] References Cited

U.S. PATENT DOCUMENTS

| 4,010,758 | 3/1977 | Rockland et al. | 128/785 |
| 4,136,701 | 1/1979 | Barton et al. | 128/419 P |
| 4,235,246 | 11/1980 | Weiss et al. | 128/419 P |

FOREIGN PATENT DOCUMENTS 1316072  5/1973  United Kingdom ................ 128/642

*Primary Examiner*—William E. Kamm
*Attorney, Agent, or Firm*—John L. Rooney; Joseph F. Breimayer; Carl A. Forest

[57] ABSTRACT

Epicardial pacing lead for affixation to epicardial heart tissue either onto the forward facing portion of the heart or behind the heart during thoracic surgery. A stylet controls a helical fixation screw in an electrode head of the pacing lead in that the stylet is turned thereby advancing the helical fixation screw beyond the planar surface of the electrode head. The epicardial pacing lead includes two embodiments which can be used in the unipolar mode of operation and one embodiment which can be used in the bipolar or unipolar mode of operation. The epicardial pacing lead requires no special tools and can be applied to the epicardial tissue with the use of surgical forceps or clamps. The pacing lead can be connected to a pulse generator located adjacent to the epicardial tissue under the skin and can be used for atrial or ventricular pacing.

5 Claims, 10 Drawing Figures

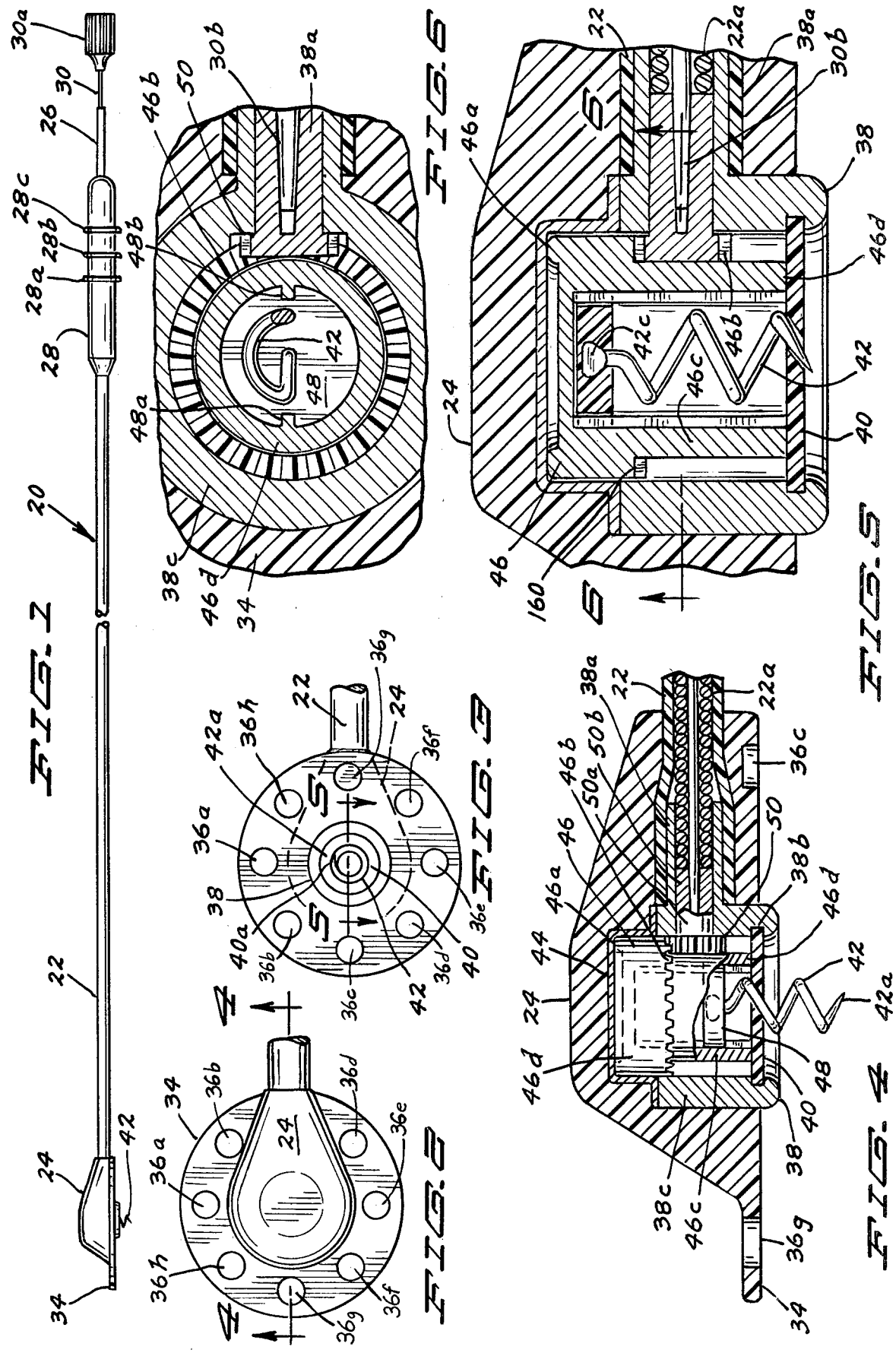

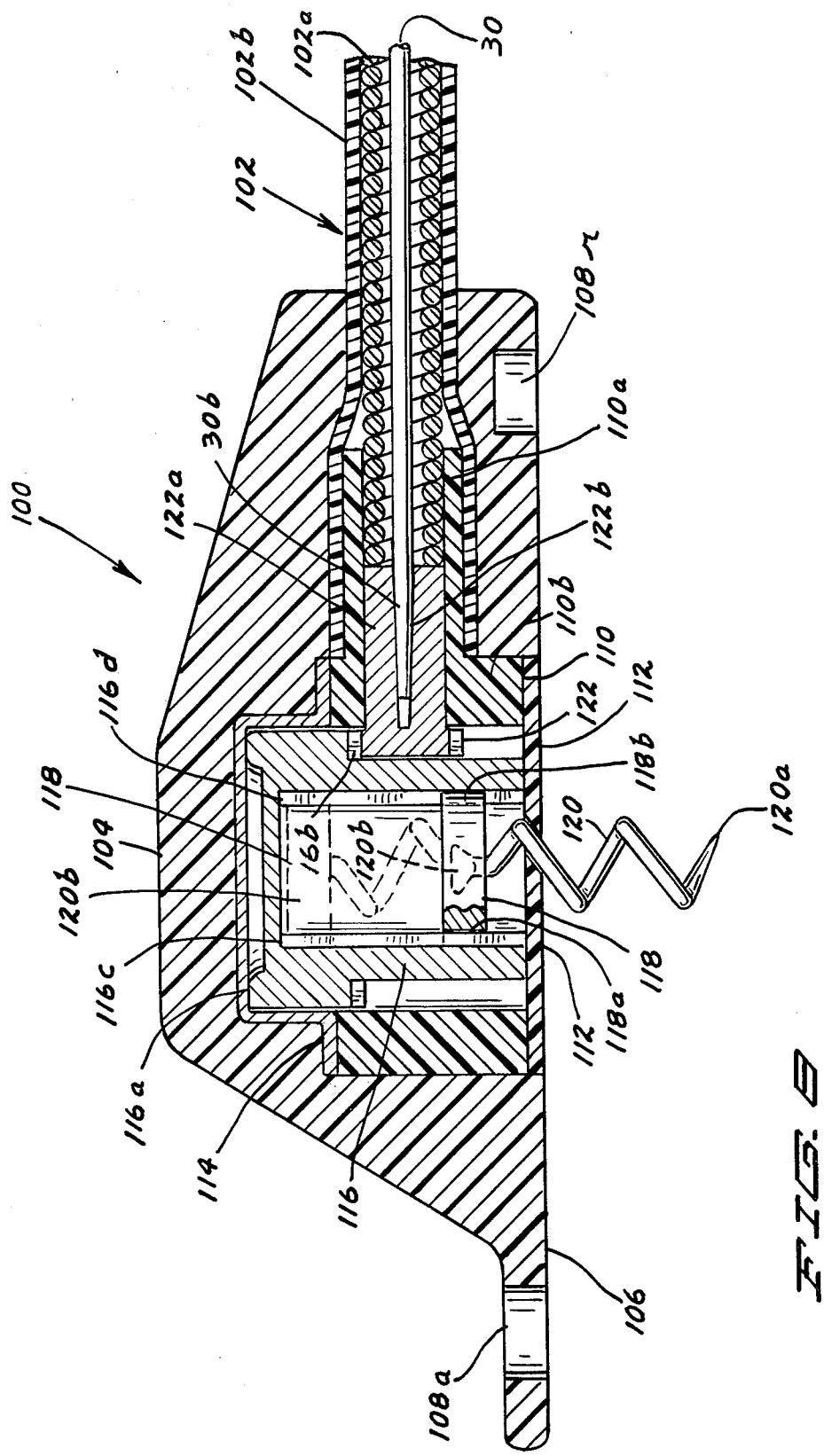

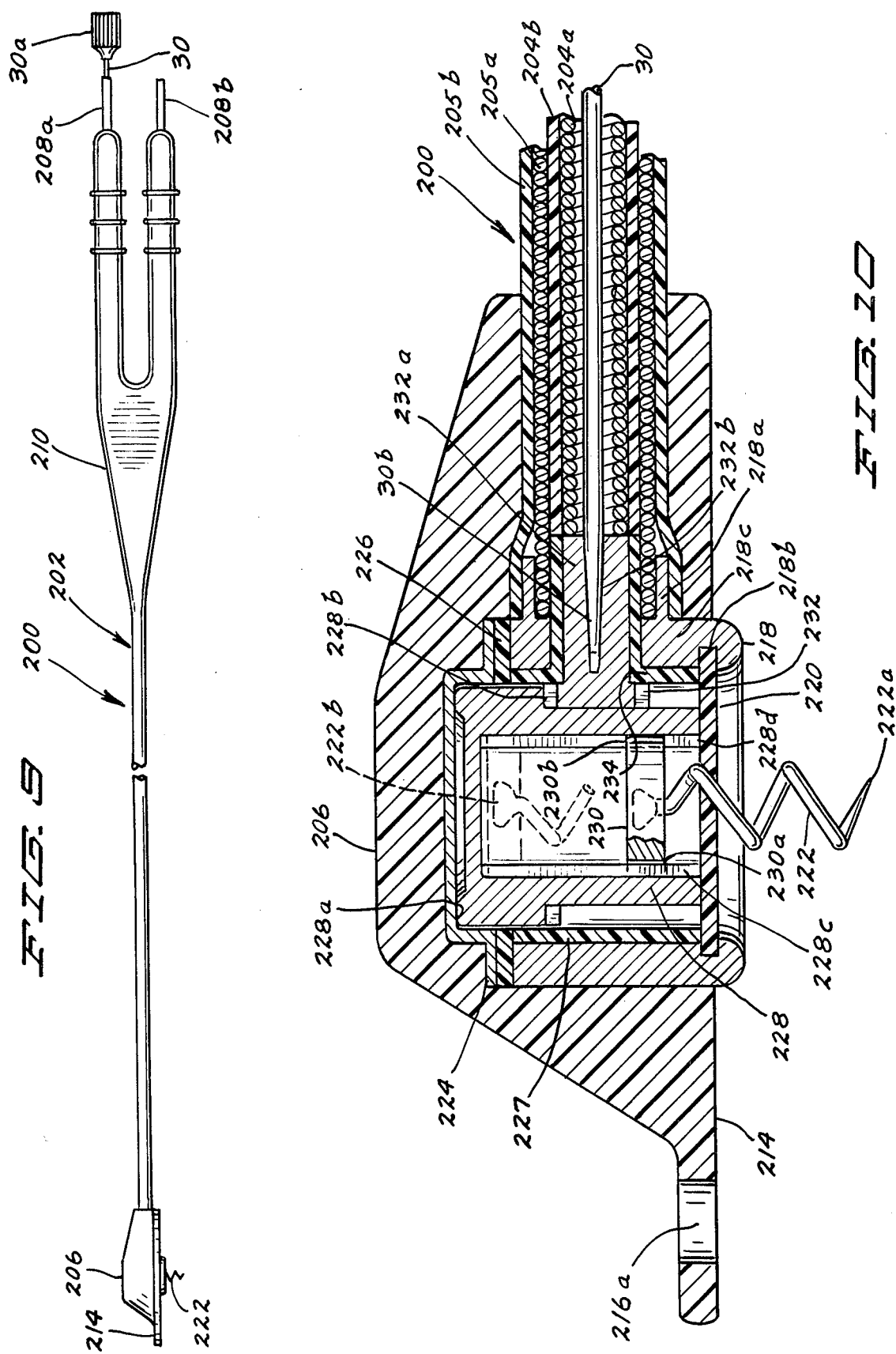

EPICARDIAL PACING LEAD WITH STYLET CONTROLLED HELICAL FIXATION SCREW

BACKGROUND OF THE INVENTION

1. Field of the Invention

The present invention relates to a surgical electrical applicator, and more particularly, pertains to an epicardial pacing lead stylet controlled helical fixation screw.

2. Background of the Invention

Prior art epicardial pacing leads have illustrated a number of disadvantages. The main and foremost disadvantage of epicardial pacing leads has been that the lead requires a special tool for affixation to the epicardial tissue. This has not only resulted in increased manufacturing expense, but also a certain degree of dexterity by the physician-surgeon affixing the lead to epicardial tissue. Another disadvantage with the prior art epicardial pacing leads is that the configuration of the electrode is sometimes extremely large, detracting from implantation areas of epicardial tissue having limited height thereby preventing affixation of the pacing lead. Also, epicardial pacing leads are not lended to positioning and pacing behind the heart. Finally, the prior art epicardial pacing leads have required a separate mapping tool prior to affixation of the epicardial pacing lead.

The present invention overcomes the disadvantages of the prior art by providing an epicardial pacing lead having a particularly low physical profile providing for affixation to areas of epicardial tissue which previously prevented affixation due to limited height and closeness of the surrounding area.

SUMMARY OF THE INVENTION

The general purpose of this invention is to provide an epicardial pacing lead with stylet controlled helical fixation screw for either unipolar or bipolar pacing in either the atrial or ventricular mode, and which requires no special surgical techniques, nor special surgical tools for affixation of the epicardial pacing lead to the epicardial tissue of the heart.

According to one embodiment of the present invention, there is provided an epicardial pacing lead having an insulated multifilar coiled conductor, a terminal pin or pins at a proximal end of the coiled conductor, and a helical fixation screw mounted in a right angled relationship in an electrode head at a distal end of the coiled conductor, the helical fixation screw mechanically coupled for rotation to a right angle gear drive in alignment with the coiled conductor, the gear drive including structure for rotation by a flat edge stylet whereby the flat edge of the stylet is inserted through a terminal pin at the proximal end, through the insulated coiled conductor, and into the gear drive assembly thereby providing for rotation of the helical fixation screw within the electrode head for subsequent affixation of the planar surface of the electrode head to the epicardial tissue of the heart. The helical fixation screw can be conductive and used in a unipolar mode of pacing or the ring electrode can surround the helical fixation screw where the helical fixation screw is nonconductive. Alternatively, the insulated coiled conductor can be coaxial where the ring electrode can be an anode and the helical fixation screw can be a cathode for the bipolar mode of pacing or vice versa.

A significant aspect and feature of the present invention is an epicardial pacing lead which does not have a helical fixation screw protruding beyond the planar surface of the electrode head until the helical fixation screw is actuated by a stylet. This is particularly beneficial for the instances where the epicardial pacing lead is secured behind the heart to the epicardial tissue or in close working areas with negligible space so that the electrode head can be positioned at a pacing location and the helical fixation screw can be subsequently screwed through use of a stylet thereby affixing the electrode head to the epicardial tissue of the heart.

Another significant aspect and feature of the present invention is an electrode head which does not require turning of the lead body or electrode head to affix the fixation screw to the epicardial tissue. This is particularly advantageous in allowing a physician-surgeon to position and secure the pacing lead at any location on the epicardial tissue of the heart.

A further significant aspect and feature of the present invention is an epicardial pacing lead with a stylet controlled helical fixation screw which provides for easy insertion and easy removal. All that is required by the physician-surgeon is to turn a stylet having a flattened tip which actuates a ring-gear assembly thereby screwing the helical fixation screw into or out of the epicardial tissue.

A further significant aspect and feature of the present invention is an epicardial pacing lead with a stylet controlled helical fixation means which requires no special tools for affixation other than a flattened tip stylet which is commonly sold. Also, the electrode head having a low physical profile and minimal height can be held against the myocardium with standard forceps or clamps while the helical fixation means is rotated and screwed into the heart.

Another significant aspect and feature of the present invention is an epicardial pacing lead with stylet controlled helical fixation screw which can be used in either the atrial or ventricular mode of pacing and can either be unipolar or bipolar as later described in detail.

Another significant aspect and feature of the present invention is an epicardial pacing lead with stylet controlled helical fixation screw where the helical fixation screw can be retracted to detach the lead from epicardial tissue as desired.

BRIEF DESCRIPTION OF THE DRAWINGS

Other objects and many of the attendant advantages of this invention will be readily appreciated as the same become better understood by reference to the following detailed description when considered in connection with the accompanying drawings, in which like reference numerals designate like parts throughout the FIGURES thereof and wherein:

FIG. 1 illustrates a plan view of a unipolar epicardial facing lead including an electrode head and with a stylet controlled helical fixation screw and a ring electrode;

FIG. 2 illustrates a top view of the electrode head;

FIG. 3 illustrates a bottom view of the electrode head;

FIG. 4 illustrates a partial cross-sectional view taken along line 4—4 of FIG. 2 as partially exposed;

FIG. 5 illustrates an enlarged cross-sectional view taken along line 5—5 of FIG. 3;

FIG. 6 illustrates a bottom plan view taken along line 6—6 of FIG. 5;

FIG. 8 illustrates an enlarged cross-sectional view of another embodiment of an epicardial pacing lead with a stylet controlled helical fixation screw including a conductive helical fixation screw;

FIG. 9 illustrates a plan view of a bipolar epicardial pacing lead with a stylet controlled helical fixation screw with a ring electrode; and FIG. 10 illustrates a cross-sectional view of the electrode head of the bipolar epicardial pacing lead of FIG. 9.

DESCRIPTION OF THE PREFERRED EMBODIMENT OF FIGS. 1-6

Figure 7:
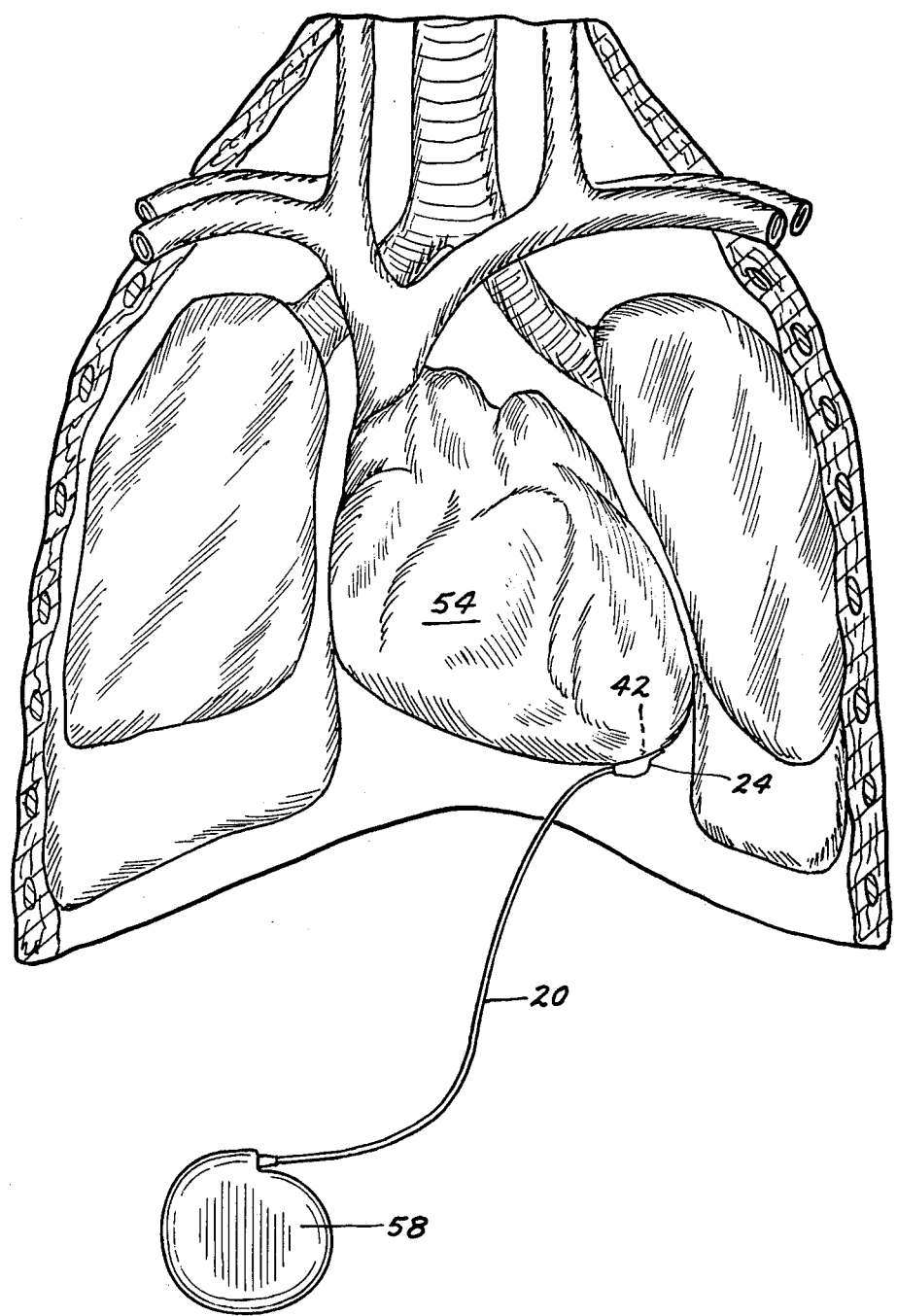
FIG. 7 illustrates a thoracic chest view of a heart having affixed thereto the electrode head of the epicardial pacing lead with the stylet controlled helical fixation screw having been positioned with surgical forceps at a pacing location of epicardial tissue and a proximal end of a coiled conductor connected to a pulse generator.

FIG. 1, which illustrates a plan view of a unipolar epicardial pacing lead 20 with a stylet controlled helical fixation screw 42, the present invention, as illustrated extending partially downward beyond an electrode head 24, shows an insulated multi-filar coiled conductor 22, the electrode head 24 connected to a distal end of the insulated coiled conductor 22 and including a fixation pad 34, a terminal pin 26 in a connector sleeve 28 including a plurality of securing rings 28a-28c connected to a proximal end of the coiled conductor 22, and a stylet wire 30 including a stylet knob 30a secured to the proximal end of a stylet wire 30. The electrode head 24, insulation 22 of the coiled conductor 22a, and fixation pad 34 can be silicon rubber, urethane, polyether urethane elastomer, or other like material by way of example and for purposes of illustration only. The coiled conductor 22a can be multi-filar nickel alloy coiled conductor such as trifilar or quadrafilar and commonly referred to as MP35N by way of example and for purposes of illustration only, and which can be manufactured under the Drawn-Brazed-Stranded (DBS) process.

FIG. 2, which illustrates a top plan view of the electrode head 24 of the pacing lead 20, shows the fixation pad 34 about the lower portion of the electrode head 24, and including a plurality of fibrous ingrowth holes 36a-36h positioned around the outer periphery of the fixation pad 34. A patch of surgical mesh can be utilized in lieu of the fixation pad 34.

FIG. 3, which illustrates a bottom plan view of the electrode head 24, shows a ring electrode 38 of platinum, platinum-iridium or other like material by way of example and for purposes of illustration only, a silicon rubber, urethane, or other like material guide seal 40, and a helical fixation screw 42 including a tip 42a. The tip 42a can protrude just slightly into or through the outer surface of the guide seal 40 if desired for starting rotation of the helical screw 42. The guide seal 40 includes a helical lumen hole 40a for permitting the tip 42a of the helical fixation screw 42 to extend partially or completely through a thin membrane. FIG. 4, which illustrates a partial cross-sectional view taken along line 4—4 of FIG. 2, shows a coiled conductor 22a covered by insulation 22, and electrically and mechanically connected to a horizontal flange 38a of the ring electrode 38 which includes vertical cylindrical member 38c. The guide seal 40 engages and is secured by adhesive, swaging, or like material into a groove 38b in the cylindrical body 38c of the ring electrode 38. A keyway can be provided in the groove 38b for locking engagement with a key of the guide seal 40 in the groove 38b as provided. A support cap 44 such as a metal cup mechanically secures such as by welding to the top of the cylindrical member 38c of the ring electrode 38 providing further support for the ring electrode 38 in the electrode head 24. A cylindrical member 46 as also illustrated in FIG. 5 axially rotates in the support cap 44 and includes a rounded top 46a, a plurality of gear teeth 46b.1-46b.n, where the number of teeth is limited by physical size and extending downwardly as illustrated in FIG. 4 and FIG. 5, and opposing longitudinal slide members 46c and 46d extending down inside of the cylindrical member 46. A disc 48 of electrical insulative material including opposing notches 48a and 48b as illustrated in FIG. 6 is in slideable engagement with the longitudinal slide members 46c and 46d. A flattened portion 42b, 42c or a close turn of the helical fixation screw 42 secures into the insulative disc 48. A gear 50 axially mounts in the flange 38a of the ring electrode 38, and includes a right angle shaft 50a having a rectangular lumen 50b for accepting a flattened end 30b of the stylet wire 30 as illustrated in FIG. 5.

FIG. 5, which illustrates an enlarged cross-sectional view taken along line 5—5 of FIG. 3, shows structure where all numerals correspond to those elements previously described.

FIG. 6, which illustrates a cross-sectional view taken along line 6—6 of FIG. 5, shows numerals which correspond to those elements previously described. The figure particularly shows the circular gear train 46b.1-46b.n, and the insulative disc 48 including notches 48a and 48b supporting the helical fixation screw 42.

PREFERRED MODE OF OPERATION

The epicardial pacing lead 20 with the stylet controlled helical fixation screw 42 is unpackaged from a sterilized package or is sterilized prior to affixation to epicardial tissue of the heart. A stylet 30 is inserted down through the multifilar insulated coiled conductor 22 so that the flat tip 30b of the stylet 30 engages into the rectangular shaft portion 50b of the gear train 50.

Either before or after the preparation of the pacing lead 20, the patient's thoracic cavity is opened for gaining direct access to the epicardial tissue of the heart 54 for suitable fixation of the electrode head 24 to the epicardial tissue.

Once the site of affixation is determined through an electrode mapping operation, the planar surface of the electrode head 24 is positioned at the site, and forceps or clamps can be used to hold the electrode head 24 in position on the epicardial tissue of the heart while activating the helical fixation screw 42 through the stylet 30 engaged through a lumen in the pacing lead 20. The ring electrode 38 can also be used for mapping of the epicardial tissue. The knob 30a of the stylet 30 is turned thereby rotating the helical fixation screw 42 into the epicardial tissue of the heart, especially for affixation to normally inaccessible areas of the heart. The wedged tip 30b rotates the gear train 50 which rotates the cylindrical member 46 respectively driving the insulative disc 48 downward toward the guide seal 40 resulting in downward motion and carrying the helical fixation screw 42 simultaneously into the heart tissue.

As the helical fixation screw 42 screws through the guide seal 40 and into the epicardial tissue, the flat circular insulative disc 48 rides downwardly on the longitudinal members 46c and 46d through the geared arrangement between gears 50 and 46b.

At fixation, the ring electrode 38 rests against epicardial tissue and is secured to the pacing site by the helical fixation screw 42. The multifilar insulated coiled conductor 22 is then routed out through the thoracic cavity and under the skin to the site of an implantable pulse generator 58 implanted under the skin. The stylet 30 is removed after affixation of the helical fixation screw 42. After fixation, fibrous ingrowth occurs up through the holes 36a-36h in the fixation pad 34.

DESCRIPTION OF ANOTHER PREFERRED EMBODIMENT OF FIG. 8

FIG. 8 illustrates an enlarged cross-sectional view of a unipolar epicardial pacing lead 100 with a stylet controlled helical fixation screw 120. This other embodiment of the present invention shows a helical fixation screw 120 as illustrated extending downward beyond an electrode head 104 having an insulated multifilar coiled conductor 102 as described previously connected thereto. The electrode head 104 connects to a distal end of the coiled conductor 102a and includes a fixation pad 106. The electrode head 104, the insulation of the coiled conductor 102, and the fixation pad 106 can be silicon rubber, urethane, or other like material by way of example and for purposes of illustration only as previously described. A plurality of fibrous ingrowth holes 108a-108n positions around the outer periphery of the fixation pad 106. The coiled conductor 102a covered by the insulation 102b electrically and mechanically connects to a horizontal flange 110a of a ring member 110 which includes vertical cylindrical member 110b. A guide seal 112 engages and is secured by adhesive or like material into the fixation pad 106 and is substantially adjacent to the cylindrical body and aligned therewith. A support cap 114 mechanically secures to the top of the cylindrical member 110b of the ring member 110 providing further support for the structure. A metal cylindrical member 116 axially rotates in the support cap 114 and in the cylindrical member 110b, and includes a rounded top 116a, a plurality of gear teeth 116b.1-116b.n extending downwardly around the member, and opposing longitudinal slide members 116c and 116d extending down inside of the cylindrical member 116. A metal disc 118 including opposing notches 118a and 118b is in slideable electrical and mechanical engagement with the longitudinal slide members 116c and 116d and can wedge into engagement at the bottom of the slide members 116c and 116d. The disc 118 is illustrated in imaginary lines in an unengaged position and in solid lines in an engaged position. A flattened portion 120b of the helical fixation screw 120 secures into the disc 118. A gear 122 axially mounts in the flange 110a of the member 110, and includes a right angle shaft 122a having a rectangular portion 122b which accepts a flattened end 30b of the stylet wire 30.

PREFERRED MODE OF OPERATION OF FIG. 8

The operation of the pacing lead 100 of FIG. 8 is identical to that of FIGS. 1-6 with the exception that the helical screw 120 is conductive in FIG. 8 while the ring electrode 38 is conductive in FIGS. 1-6.

Prior to affixation of the pacing lead 100 to epicardial tissue of the heart, a mapping electrode can be utilized to determine the preferred point of affixation for optimum results.

DESCRIPTION OF A FURTHER PREFERRED EMBODIMENT OF FIGS. 9-10

FIG. 9 illustrates a plan view of a bipolar epicardial pacing lead 200 with a stylet controlled helical fixation screw 222. This further embodiment of the present invention shows a helical fixation screw 222 as illustrated extending downward beyond an electrode head 206 having an insulated multifilar coiled coaxial conductor 202 connected thereto. The electrode head 206 connects to a distal end of the insulated coaxial conductor 202 and includes a fixation pad 214. Terminal pins 208a and 208b in a connector sleeve 210 including a plurality of securing rings connect to the proximal end of the insulated coaxial conductor 202. A stylet wire 30 including a stylet knob 30a engages into a hole through a terminal pin 208a. The electrode head 206, insulated coiled conductor insulation 202, and the fixation pad 214 can be silicon rubber, urethane, or other like material by way of example and for purposes of illustration only as described in the previous embodiments.

FIG. 10, which illustrates an enlarged cross-sectional view of the electrode head 206, shows coaxial multifilar inner and outer coiled conductors 205a and 204a respectively and covered by insulation 205b and 204b respectively where the conductors are electrically and mechanically connected to a horizontal flange 218a of the ring electrode 218 which includes vertical cylindrical member 218c, and right angle shaft 232a, respectively. A guide seal 220 engages and secures by adhesive, swaging or like method into a groove 218b in the cylindrical body 218c of the ring electrode 218. A keyway can be provided in the groove 218b for locking engagement of the guide seal 220 in the groove 218b as predetermined. A support cap 224 secures to the top of the cylindrical member 218c of the ring electrode 218 with insulation 226 therebetween and provides further support for the ring electrode 218 structure. Insulation 227 is also provided between ring electrode 218 and a cylindrical member 228. The cylindrical member 228 axially rotates in the support cap 224 and in the cylindrical member 218c and includes a rounded top 228a, a plurality of gear teeth 228b.1-228b.n extending downwardly as illustrated and opposing longitudinal slide members 228c and 228d. A metal disc 230 includes opposing notches 230a and 230b and is in slideable electrical and mechanical engagement with the longitudinal slide members 228c and 228d. The disc 230 is illustrated in dashed lines in an unengaged position and in solid lines in an engaged position. A flattened portion 222b of the helical fixation screw 222 secures into the disc 230. A metal gear 232 axially mounts in an insulative member 234, and includes a right angle shaft 232a having a flattened portion 232b for accepting a flattened end 30b of the stylet wire 30 as illustrated in the figure.

PREFERRED MODE OF OPERATION OF FIGS. 9-10

The bipolar epicardial pacing lead 200 is affixed to the epicardial tissue of the heart as previously described.

Prior to affixation of the pacing lead 200, a mapping electrode can be utilized to determine the preferred point of affixation for optimum results.

Various modifications can be made to the present invention without departing from the apparent scope thereof.

A physician may choose to connect the lead of FIGS. 9-10 to a bipolar pulse generator or may choose to connect one or the other of the pins to a unipolar pulse generator. In this mode of operation, the fixation helix of the ring of the bipolar version may be used as the active electrode and the other connector pin would be covered with a rubber boot. Thus the lead can be advantageously used for either unipolar or bipolar pacing.

Any suitable mechanical drive mechanism can be utilized for rotating the helical coils such as a flexible coil, splined shaft, etc., and is not construed to be limited to the present gear assembly.

Having thus described the present invention, what is claimed is:

1. A body implantable lead comprising:
  a conductor having proximal and distal ends;
  an insulating sheath of body compatible materials covering said conductor;
  a stylet removably located within said insulating sheath;
  an electrode housing attached to said distal end of said conductor;
  a fixation helix having a pointed tip rotatably attached to said electrode housing at an angle substantially perpendicular to the longitudinal axis of said stylet; and
  means within said electrode housing for transmitting torque from said stylet to said fixation helix whereby rotation of said stylet causes said fixation helix to rotate.

2. A body implantable lead according to claim 1 wherein said distal end of said conductor is electrically coupled to said fixation helix.

3. A body implantable lead according to claim 2 wherein said conductor further comprises a coil having an interior lumen.

4. A body implantable lead according to claim 3 wherein said stylet is removably located within said interior lumen.

5. A body implantable lead according to claim 4 wherein said torque transmitting means further comprises:
  a first gear detachably coupled to said stylet which rotates in a first plane perpendicular to the longitudinal axis of said stylet; and
  a second gear rotatably coupled to said first gear and coupled to said fixation helix mounted to rotate in a second plane perpendicular to said first plane.

* * * * *